United States Patent [19]
Rodriguez et al.

[11] Patent Number: 5,463,090
[45] Date of Patent: Oct. 31, 1995

[54] INTEGRATED PROCESS FOR EPOXIDE PRODUCTION

[75] Inventors: Carmen L. Rodriguez, Exton; John G. Zajacek, Devon, both of Pa.

[73] Assignee: Arco Chemical Technology, L.P., Greenville, Del.

[21] Appl. No.: 330,057

[22] Filed: Oct. 27, 1994

[51] Int. Cl.$^6$ .................. C07D 301/12; C07D 303/04
[52] U.S. Cl. ............................................ 549/531
[58] Field of Search ............................. 549/531

[56] References Cited

U.S. PATENT DOCUMENTS

| | | | |
|---|---|---|---|
| 4,342,700 | 8/1982 | Sakai et al. | 260/370 |
| 4,833,260 | 5/1989 | Neri et al. | 549/531 |
| 5,166,372 | 11/1992 | Crocco et al. | 549/531 |
| 5,214,168 | 5/1993 | Zajauk et al. | 549/531 |
| 5,221,795 | 6/1993 | Clerici et al. | 549/531 |
| 5,252,758 | 10/1993 | Clerici et al. | 549/531 |
| 5,262,550 | 11/1993 | Crocco et al. | 549/531 |
| 5,384,418 | 1/1995 | Zojacek et al. | 549/531 |

FOREIGN PATENT DOCUMENTS

| | | |
|---|---|---|
| 673355 | 10/1963 | Canada . |
| 0526945 | 2/1993 | European Pat. Off. . |
| 0549013 | 6/1993 | European Pat. Off. . |
| 1256598 | 2/1961 | France . |
| 803121 | 10/1958 | United Kingdom . |
| 834264 | 5/1960 | United Kingdom . |

*Primary Examiner*—Joseph E. Evans
*Attorney, Agent, or Firm*—Stephen D. Harper

[57] ABSTRACT

Epoxides are produced by an integrated process involving molecular oxygen oxidation of an alkylammonium salt of a sulfonic acid-substituted anthrahydroquinone, epoxidation of an ethylenically unsaturated substrate using the hydrogen peroxide-containing product obtained by such oxidation in the presence of a titanium silicalite catalyst, and regeneration of the anthrahydroquinone by hydrogenation of the anthraquinone co-product. Oxidation and epoxidation may be performed concurrently. The alkylammonium salts have the advantage of being highly soluble in polar protic media such as water and lower alcohols.

24 Claims, 1 Drawing Sheet

INTEGRATED PROCESS FOR EPOXIDE PRODUCTION

FIELD OF THE INVENTION

This invention relates to an integrated process for producing an epoxide. In particular, the invention pertains to a process whereby an alkyl ammonium salt of a sulfonic acid-substituted anthrahydroquinone is oxidized with molecular oxygen to afford an oxidation reaction product containing hydrogen peroxide and the corresponding anthraquinone salt. The oxidation reaction product is used to epoxidize an olefin, wherein the epoxidation is catalyzed by a titanium silicalite. Regeneration of the anthrahydroquinone is accomplished by hydrogenation. Due to the surprisingly high solubility of the alkyl ammonium salts in solvents such as water and alcohols, reactor volumes may be advantageously minimized.

BACKGROUND OF THE INVENTION

Many different methods for the preparation of epoxides have been developed. One such method involves the use of certain titanium silicalite materials to catalyze olefin oxidation by hydrogen peroxide. This method is described, for example, in Huybrechts et al., *J. Mol. Catal.* 71,129(1992), U.S. Pat. Nos. 4,824,976 (Clerici et al.) and 4,833,260 (Neri et al.), European Pat. Pub. Nos. 311,983, 190,609, 315,247 and 315,248, Belgian Pat. Pub. No. 1,001,038, Clerici et al., *J. Catal.* 129,159(1991), and Notari, in "Innovation in Zeolite Material Science," *Studies in Surface Science and Catalysts*, vol. 37, p. 413 (1988).

The prior art related to titanium silicalite-catalyzed epoxidation teaches that it is beneficial to employ a hydrogen peroxide solution that does not contain large amounts of water and recommends the use of an organic solvent as a liquid medium for the epoxidation reaction. For example, European Patent Publication No. 526,945 describes a process for producing epoxides wherein hydrogen peroxide is generated in situ by reacting oxygen or air with a redox system comprising alkyl-substituted anthraquinone in the presence of the olefin to be epoxidized, titanium silicalite catalyst, and a specific type of solvent mixture consisting of one or more particular aromatic hydrocarbons, one or more particular relatively high boiling polar organic compounds, and a low molecular weight alcohol. The precise reasons for preferring such a complex solvent mixture are not enumerated by the publication, but it is well-known that alkyl-substituted anthraquinones and alkyl-substituted anthrahydroquinones have poor solubility in many common solvents (placing an upper limit on the maximum amount of hydrogen peroxide which can be generated in a given reactor volume). In other common solvents, poor selectivities during oxidation or reduction are observed due to competing reactions of the solvent.

European Patent Publication No. 549,013 teaches a process for epoxidizing olefins with hydrogen peroxide in the presence of titanium silicalite wherein a water-alcohol solvent mixture is used to extract the hydrogen peroxide produced in a redox process with alkyl-substituted anthraquinone. The water-alcohol solvent mixture is recycled following epoxidation. As discussed previously, such alkyl-substituted anthraquinones have relatively limited solubilities in organic solvents, thereby placing significant restraints on the commercial utility of the process.

The use of certain water-soluble anthraquinones to avoid solubility limitations in hydrogen peroxide processes has been proposed. For example, British Pat. No. 834,264 and French Pat. No. 1,256,598 teach that the alkali metal, alkaline earth metal, and ammonium salts of anthraquinone-2,7-disulfonic acid could be employed to manufacture hydrogen peroxide. Unfortunately, such salts have somewhat limited solubility in water (i.e., $\leq 300$ g/L) and thus do not offer any substantial advantages over the conventional organic solvent-soluble anthraquinones.

SUMMARY OF THE INVENTION

We have now unexpectedly discovered that by forming the alkylammonium salt of a sulfonic acid-substituted anthraquinone, the solubility of such a species in water, alcohols, and the like may be significantly enhanced. This surprising improvement in solubility makes possible the production of much higher hydrogen peroxide concentrations in an anthraquinone autoxidation process than had heretofore been feasible with the corresponding alkali metal, alkaline earth metal, or ammonium ($NH_4$) salts. The oxidation product thereby obtained is suitable for use as a source of hydrogen peroxide in a titanium silicalite-catalyzed epoxidation of an olefin; no prior treatment or fractionation of the oxidation product is required.

The invention provides an integrated process for producing an epoxide comprising reacting a sulfonic acid-substituted anthrahydroquinone alkylammonium salt with molecular oxygen to form an oxidation reaction product comprised of hydrogen peroxide and a sulfonic acid-substituted anthraquinone alkylammonium salt. In a subsequent step or concurrent with the foregoing oxidation step, the oxidation reaction product is contacted with an ethylenically unsaturated substrate and a catalytically effective amount of a titanium silicalite at a temperature effective to form an epoxidation reaction mixture comprised of the sulfonic acid-substituted anthraquinone alkylammonium salt and the epoxide. The epoxide is separated from the sulfonic acid-substituted anthraquinone alkylammonium salt. The latter component is reacted with hydrogen in the presence of a hydrogenation catalyst wherein said hydrogenation catalyst preferably is heterogeneous and is suitably comprised of a transition metal selected from palladium, platinum, ruthenium, chromium, rhodium, and nickel to regenerate the sulfonic acid-substituted anthrahydroquinone alkylammonium salt. The regenerated salt is recycled for use in the molecular oxygen oxidation step.

DETAILED DESCRIPTION OF THE INVENTION

Figure 1:
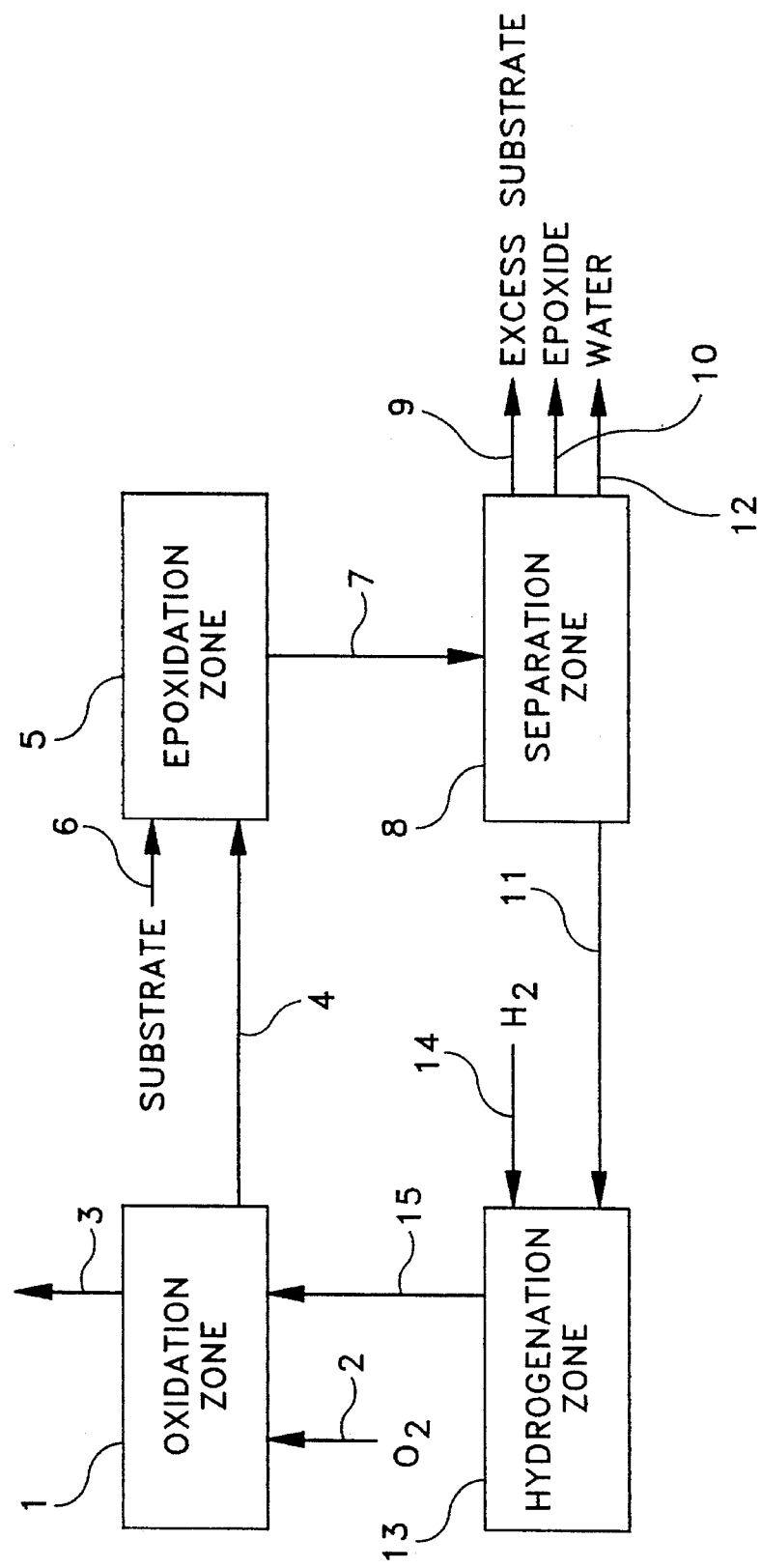
FIG. 1 is a schematic representation illustrating one embodiment of the process of the invention, to be explained in more detail hereinafter.

Sulfonic acid-substituted anthrahydroquinones suitable for use (in alkylammonium salt form) in the process of this invention include the class of organic substances containing both an anthrahydroquinone moiety and at least one sulfonic acid group ($—SO_3H$) pendent thereto. Such substances are well known and are obtainable by direct sulfonation of the corresponding anthraquinone and subsequent hydrogenation. See, for example, Fierz-David et al., *Helv. Chim. Acta*, 10, 221 (1927). The sulfonic acid group(s) are preferably attached directly to the aromatic nuclei of the anthrahydroquinone, but may also be attached via intermediary groups such as methylene and the like. Preferably, at least two sulfonic acid groups per anthrahydroquinone molecule are present. Each anthrahydroquinone molecule may, for example, be substituted with two, three, four, or more sulfonic acid groups. The anthrahydroquinone may also bear other substituents such as hydrogen, alkyl, aryl, acyl, ester, alkoxy, halide, and like groups, provided such substituents do not interfere with the desired oxidation/reduction reactions of the sulfonic acid-substituted anthrahydroquinone alkylammonium salt.

The sulfonic acid groups are converted into salt form wherein the cation is an alkylammonium species. For reasons which are not well understood, such salts generally have a much greater solubility in protic polar solvents such as water and methanol than the corresponding acid, ammonium ($NH_4$), alkali metal, or alkaline earth metal salt forms of such compounds. Additionally, the salts employed in the present process are considerably less acidic than the free sulfonic acid form of the anthrahydroquinone and thus exhibit minimal tendency to promote non-selective ring opening reactions of the epoxide formed during the epoxidation step of the process. Preferably, the alkyl groups in such alkyl ammonium species are selected from lower alkyl groups (e.g., $C_1$–$C_6$), but most preferably are selected from methyl, ethyl, n-propyl, isopropyl, n-butyl, sec-butyl, isobutyl, tert-butyl, or combinations thereof. For example, the alkylammonium cation may be tetramethylammonium, tetraethylammonium, or tetrabutylammonium. The alkylammonium cation may have from 1 to 4 alkyl groups substituted on the nitrogen atom. The alkyl groups attached to nitrogen may be the same or different.

The alkylammonium salts preferably have the structure

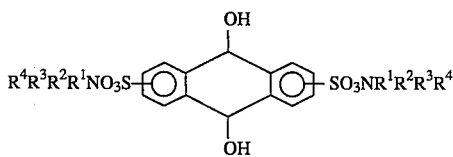

wherein $R^1$, $R^2$, $R^3$, and $R^4$ are the same or different and are selected from the group consisting of hydrogen and $C_1$–$C_6$ alkyl, subject to the proviso that at least one of $R^1$, $R^2$, $R^3$, or $R^4$ is $C_1$–$C_6$ alkyl. Preferably, the total number of carbon atoms in $R^1$, $R^2$, $R^3$ and $R^4$ is from 4 to 16. Generally speaking, as the number of carbon atoms is increased, the solubility of the salt in alcohols such as methanol increases and the solubility in water decreases. The maximum concentration of a given salt in a liquid medium (and thus the maximum $H_2O_2$ concentration obtainable) may be readily optimized by adjusting the solvent system employed. The —$SO_3NR_4$ groups may be placed on any of the four available sites on each aromatic nucleus, with the other sites being preferably occupied by hydrogen (—H). Illustrative sulfonic acid-esterified anthrahydroquinones which may be used to prepare suitable alkylammonium salts include, but are not limited to, anthrahydroquinone-1,5-disulfonic acid, anthrahydroquinone-1,7-disulfonic acid, anthrahydroquinone-2,6-disulfonic acid, anthrahydroquinone-2-sulfonic acid, anthrahydroquinone-1,8-disulfonic acid, anthrahydroquinone-2,5-disulfonic acid, anthrahydroquinone-2,7-disulfonic acid, and the like.

The alkylammonium salt of the sulfonic acid-substituted anthrahydroquinone is preferably reacted with molecular oxygen in a liquid medium. The liquid medium preferably is comprised of a polar protic solvent. Examples of suitable polar protic solvents include water and $C_1$–$C_6$ aliphatic alcohols (e.g., methanol, ethanol, tertiary butyl alcohol). The solvent(s) selected are preferably inert under the conditions used in the oxidation, epoxidation and hydrogenation steps of the instant process. In one desirable embodiment of the invention, the volume of liquid medium utilized is minimized relative to the amount of anthrahydroquinone/anthraquinone but is still sufficient to fully dissolve or solubilize the anthrahydroquinone/anthraquinone. The concentration of hydrogen peroxide in the oxidation reaction product and thus the overall productivity of the process will thereby be maximized.

The reaction with molecular oxygen may be performed under conditions similar to those employed in conventional hydrogen peroxide processes involving an anthrahydroquinone species. Air, pure oxygen, or pure oxygen admixed or diluted with another gas such as nitrogen may serve as a source of molecular oxygen. Generally speaking, optimum reaction rates and selectivities may be achieved by operating at a temperature of from 0° C. to 100° C. (preferably, 20° C. to 60° C.) and a partial oxygen pressure of from 0.5 to 200 psia (preferably, 1 to 20 psia). The oxidation is preferably carried out in the liquid phase, with the molecular oxygen preferably being sparged or otherwise introduced into the liquid medium containing the dissolved anthrahydroquinone salt. To minimize side reactions, such as the formation of oxidized anthraquinone by-products, the contact time of the salt with oxygen is preferably limited (typically, less than about 30 minutes). In general, it will be desirable to achieve anthrahydroquinone conversions of from 30 to 90%. The optimum contact time will be dependent upon the oxygen partial pressure, temperature, anthrahydroquinone salt reactivity, among other factors, but may be readily determined by routine experimentation. No catalyst is necessary to obtain the desired conversion of molecular oxygen to hydrogen peroxide. The amount of oxygen used should preferably be such as to avoid the explosive range while maintaining an equimolar quantity, or moderate molar excess of oxygen relative to anthrahydroquinone.

The oxidation reaction product thereby obtained will typically comprise hydrogen peroxide and the sulfonic acid-substituted anthraquinone alkylammonium salt corresponding to the starting sulfonic acid-substituted anthrahydroquinone alkylammonium salt as well as solvent and unreacted anthrahydroquinone salt. Hydrogen peroxide concentrations of 5 weight percent or greater are possible to achieve during the oxidation step of the process of this invention.

In the epoxidation step of the process of this invention, the oxidation reaction product is contacted with an ethylenically unsaturated substrate and a catalytically effective amount of a titanium silicalite, preferably at a temperature of from 0° C. to 120° C. (more preferably, 30° C. to 90° C.), to convert the substrate to the desired epoxide.

Although the oxidation reaction product could first be treated or purified prior to use in epoxidation (for example, a basic ion exchange resin could be used to remove organic acids), an important advantage of the present invention is that such pretreatment is not necessary in order to attain satisfactory yields of epoxide. In an alternative embodiment of the invention, the oxidation of the anthrahydroquinone alkylammonium salt and the epoxidation of the ethylenically unsaturated substrate are performed concurrently by generating hydrogen peroxide in situ. The sulfonic acid-substituted anthrahydroquinone alkylammonium salt thus may be reacted with molecular oxygen and the ethylenically unsaturated substrate in the presence of a titanium silicalite, preferably at a temperature of from 0° C. to 120° C. (more preferably 10° C. to 80° C.), to form an epoxidation reaction mixture comprised of the sulfonic acid-substituted anthraquinone alkylammonium salt corresponding to the anthrahydroquinone salt and the epoxide.

The ethylenically unsaturated substrate epoxidized in the process of this invention is preferably an organic compound having from two to ten carbon atoms and at least one ethylenically unsaturated functional group (i.e., a carbon-carbon double bond) and may be a cyclic, branched or straight chain aliphatic olefin. More than one carbon-carbon double bond may be present in the olefin; dienes, trienes, and other polyunsaturated substrates thus may be used.

Exemplary olefins suitable for use in the process of this invention include ethylene, propylene, the butenes, butadiene, the pentenes, isoprene, 1-hexene, 3-hexene, 1-heptene, 1-octene, diisobutylene, 1-nonene, the trimers and tetramers of propylene, cyclopentene, cyclohexene, cycloheptene, cyclooctene, cyclooctadiene, dicyclopentadiene, methylenecyclopropane, methylenecyclopentane, methylenecyclohexane, vinylcyclohexane, and vinyl cyclohexene.

Mixtures of olefins may be epoxidized and the resulting mixture of epoxides either employed in mixed form or separated into the different component epoxides.

The process of this invention is especially useful for the epoxidation of $C_2$–$C_{10}$ olefins having the general structure

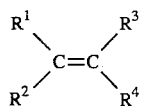

wherein $R^1$, $R^2$, $R^3$, and $R^4$, are the same or different and are selected from the group consisting of hydrogen and $C_1$–$C_8$ alkyl (selected so that the total number of carbons in the olefin does not exceed 10).

The process of this invention is also suitable for use in epoxidizing ethylenically unsaturated substrates containing functional groups other than aliphatic hydrocarbyl moieties. For example, the carbon-carbon double bond can be substituted with groups such as —$CO_2H$, —$CO_2R$, —CN, or –OR wherein R is an alkyl, cycloalkyl, aryl or aralkyl substituent. The radicals $R^1$, $R^2$, $R^3$, and $R^4$ in the structural formula shown hereinabove may contain aryl, aralkyl, halo, nitro, sulfonic, cyano, carbonyl (e.g., ketone, aldehyde), hydroxyl, carboxyl (e.g., ester, acid) or ether groups. Examples of ethylenically unsaturated substrates of these types include allyl alcohol, styrene, allyl chloride, allyl methyl ether, allyl phenyl ether, methyl methacrylate, acrylic acid, methyl acrylate, stilbene, and the like.

Although the molar ratio of substrate to hydrogen peroxide is not critical, in general it will be desirable for practical reasons to operate at a molar ratio of from 10:1 to 1:10.

The titanium silicalites useful as heterogeneous catalysts in the epoxidation step of the process comprise the class of crystalline zeolitic substances wherein titanium is substituted for a portion of the silicon or aluminum atoms in the lattice framework of a silicalite or aluminosilicate molecular sieve. Titanium silicalites are characterized by their insolubility in organic media. Such substances are well-known in the art and are described, for example, in U.S. Pat. Nos. 4,410,501 (Taramasso et al.), 4,824,976 (Clerici et al.), 4,666,692 (Taramasso et al.), Thangaraj et al., *J. Catal.* 130 1 (1991), Reddy et al., Reddy et al., *Zeolites* 12, 95 (1992), Belgian Pat. Pub, No. 1,001,038 (Bellussi et al.), Huybrechts et al., *J. Mol. Catal.* 71,129 (1992), Huybrechts et al., *Catal. Letter* 8, 237 (1991), U.S. Pat. Nos. 4,656,016 (Taramasso et al.), 4,859,785 (Bellussi et al.), 5,082,641 (Popa et al.), Clerici et al., *J. Catal.* 129,159 (1991), European Pat. Pub. No. 543,247 (Mueller et al.), Bellussi et al., *J. Catal.* 133,220 (1992), Szostak, *Molecular Sieves-Principles of Synthesis and Identification*, pp. 250–252 (1989), Tuel et al., *Zeolites*, 13, 357–364 (1993), Tuel et al., *Zeolites*, 13, 454–461 (1993), Uguina et al., *J. Chem Soc., Chem. Commun.*, 147–148 (1994), and Notari, "Synthesis and Catalytic Properties of Titanium Containing Zeolites", *Innovation in Zeolite Materials Science*, Grobet et al., Eds., 413 (1988). The teaching of these publications are incorporated herein by reference in their entirety.

Particularly preferred titanium silicalites include the classes of molecular sieves commonly referred to as "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta such as those described in U.S. applications Ser. Nos. 08/172,404 and 08/172,405, filed Dec. 23, 1993, Camblor et al., *Heterogeneous Catalysis and Fine Chemicals* III, 393–399 (1993), PCT Publication No. WO 94/02245, French Pat. Doc. No. 2,694,549, and U.S. Pat. Nos. 4,892, 720, 5,098,687, 5,233,097, and 5,271,761. The titanium silicalite preferably contains no atoms other than oxygen, titanium and silica in the lattice framework, although minor amounts of boron, iron, aluminum, phosphorus and the like may be present. For example, the titanium silicalites described in Reddy et al., *J. Catalysis*, 145, 73–78 (1994) are suitable for use.

Epoxidation catalysts suitable for use in the process of this invention will typically have a composition corresponding to the following empirical formula $xTiO_2$: $(1-x)SiO_2$, where x is between 0.0001 and 0.500. More preferably, the value of x is from 0.01 to 0.125. The molar ratio of Si:Ti in the lattice framework of the titanium silicalite is advantageously from 9.5:1 to 99:1 (most preferably, from 9.5:1 to 60:1). The use of relatively titanium-rich silicalites, such as those described in Thangaraj et al., *J. Catalysis* 130, 1–8 (1991), may also be desirable.

The amount of catalyst employed is not critical, but should be sufficient so as to substantially accomplish the desired epoxidation reaction in a practicably short period of time. The optimum quantity of catalyst will depend upon a number of factors including reaction temperature, substrate reactivity and concentration, hydrogen peroxide concentration, type and concentration of organic solvent as well as catalyst activity and the type of reactor or reaction system employed. In a batch-type or slurry reaction, for example, the amount of catalyst will typically be from 0.0001 to 10 grams per mole of substrate. In a fixed bed system, the optimum quantity of catalyst will be influenced by the flow rate of reactants through the fixed bed (typically, from about 0.05 to 2.0 kilograms hydrogen peroxide per kilogram catalyst per hour). The concentration of titanium in the total epoxidation reaction mixture will generally be from about 10 to 10,000 ppm.

The catalyst may be utilized in powder, pellet, microspheric, extruded, monolithic or any other suitable physical form. The use of a binder (co-gel) or support in combination with the titanium silicalite may be advantageous. Supported or bound catalysts may be prepared by the methods known in the art to be effective for zeolite catalysts in general. Preferably, the binder or support is essentially non-acidic and does not catalyze the non-selective decomposition of hydrogen peroxide or ring-opening of the epoxide product.

Illustrative binders and supports include silica, alumina, silica-alumina, silica-titania, silica-thoria, silica-magnesia, silica-zironia, silica-beryllia, and ternary compositions of silica with other refractory oxides. Also useful are clays such as montmorillonites, koalins, bentonites, halloysites, dickites, nacrites, and ananxites. The proportion of titanium silicalite:binder or support may range from 99:1 to 1:99, but preferably is from 5:95 to 80:20. The methods described in U.S. Pat. No. 4,701,428 (incorporated herein by reference in its entirety) may be adapted for the preparation of microspheres containing oligomeric silica binder and titanium silicalite crystals which are suitable for use in the process of this invention. Similarly, the titania-supported catalysts described in U.S. Pat. No. 5,354,875 may be employed.

The catalyst may be treated with an alkaline (basic) substance or a silylating agent so as to reduce the surface acidity, as described in U.S. Pat. No. 4,937,216. In one embodiment of this invention, the titanium silicalite catalyst is deployed in the form of a fixed bed within the reactor. In another embodiment, the catalyst is deployed in the form of a slurry. To catalyze the desired epoxidation reaction, the solid catalyst should be contacted with both the ethylenically unsaturated substrate and the hydrogen peroxide in a liquid phase. The liquid medium used for oxidation of the sulfonic-acid substituted anthraquinone alkyl ammonium salt may advantageously be utilized for epoxidation. Particularly favorable epoxidation results are obtained where the liquid medium comprises methanol.

The epoxidation reaction temperature is preferably from 0° C. to 120° C. (more preferably, 30° C. to 90° C.), which in the process of this invention has been found to be sufficient to accomplish selective conversion of the ethylenically unsaturated substrate to epoxide within a reasonably short period of time with minimal non-selective decomposition of the hydrogen peroxide. It is generally advantageous to carry out the reaction to achieve as high a hydrogen peroxide conversion as possible, preferably at least 50%, more preferably at least 90%, most preferably at least 99%, consistent with reasonable selectivities. The optimum reaction temperature will be influenced by catalyst concentration and activity, substrate reactivity, reactant concentrations, and type of solvent employed, among other factors. Reaction or residence times of from about 10 minutes to 48 hours will typically be appropriate, depending upon the above-identified variables. The reaction is preferably performed at atmospheric pressure or at elevated pressure (typically, between 1 and 100 atmospheres). Generally, it will be desirable to maintain the reaction components as a liquid mixture. For example, when an olefin such as propylene having a boiling point at atmospheric pressure which is less than the epoxidation temperature is used, a superatmospheric pressure sufficient to maintain the desired concentration of propylene in the liquid phase is preferably utilized.

The epoxidation step of this invention may be carried out in a batch, continuous, or semi-continuous manner using any appropriate type of reaction vessel or apparatus such as a fixed bed, transport bed, stirred slurry or CSTR reactor. Particularly preferred for use is the catalytic converter described in U.S. application Ser, No. 08/171,144, filed Dec. 30, 1993. Known methods of conducting metalcatalyzed epoxidations using hydrogen peroxide will generally also be suitable for use. Thus, the reactants may be combined all at once or sequentially. For example, the hydrogen peroxide and/or the substrate may be added incrementally to the reaction zone.

Once the epoxidation has been carried out to the desired degree of conversion, the epoxide product may be separated and recovered from the epoxidation reaction mixture using any appropriate technique such as fractional distillation, extractive distillation, liquid-liquid extraction, crystallization, or the like. The use of distillative methods is particularly preferred where the epoxide is relatively light (e.g., a $C_2$–$C_6$ epoxide) as the other components of the reaction mixture (except unreacted substrate) will generally be higher boiling. The epoxide thus may readily be removed as an overhead stream and the bottom fraction taken on to hydrogenation. After separating from the epoxidation reaction mixture by any suitable method such as filtration (as when a slurry reactor is utilized, for example), the recovered titanium silicalite catalyst may be economically re-used in subsequent epoxidations. Where the catalyst is deployed in the form of a fixed bed, the epoxidation product withdrawn as a stream from the epoxidation zone will be essentially catalyst free with the catalyst being retained within the epoxidation zone. Similarly, any unreacted substrate or hydrogen peroxide may be separated and recycled or otherwise disposed of. In certain embodiments of the instant process where the epoxide is produced on a continuous basis, it may be desirable to periodically or constantly regenerate all or a portion of the used catalyst in order to maintain optimum activity and selectivity. Suitable regeneration techniques are well-known and include, for example, calcination and solvent treatment.

Following epoxide removal, the sulfonic acid-substituted anthraquinone alkyl ammonium salt in the epoxidation reaction product is reacted with hydrogen in the presence of a transition metal hydrogenation catalyst under conditions effective to convert all or a portion of the anthraquinone salt to the corresponding anthrahydroquinone salt.

Methods of converting anthraquinones to their corresponding anthrahydroquinones by catalytic hydrogenation using a transition metal catalyst and hydrogen gas are well-known and are generally described, for example, in the following publications (incorporated herein by reference in their entirety): Freifelder, *Catalytic Hydrogenation Organic Synthesis-Procedures and Commentary*, Wiley-Interscience (1978), Augustine, *Catalytic Hydrogenation Techniques and Applications in Organic Synthesis* M. Dekker (1965), Freifelder, *Practical Catalytic Hydrogenation: Techniques and Applications* Wiley-lnterscience (1971), Keiboom, *Hydrogenation and Hydrogenolysis in Synthetic Organic Chemistry*, Delft University Press (1977), and Peterson, *Hydrogenation Catalysts*, Noyes Data Corp. (1977).

The hydrogenation conditions described in French Pat. No. 1,256,598, and British Pat. No. 803,121 and 834,264 are especially suitable for use in the present invention.

The transition metal in the hydrogenation catalyst is preferably palladium, platinum, chromium (as in copper chromite, for example), rhodium, nickel, or ruthenium. The use of a supported palladium catalyst is especially advantageous. The hydrogenation is most suitably carried out in a liquid phase. As water will generally be present in the epoxidation reaction mixture, the catalyst employed should be tolerant of water (i.e., it should not lose activity upon prolonged contact with water).

The temperature, hydrogen pressure, and catalyst concentration during hydrogenation are selected so as to accomplish substantial (i.e., at least 80% and more preferably at least 98%) conversion of the anthraquinone salt to the anthrahydroquinone salt within a practicably shod reaction time (i.e., approximately 15 minutes to 12 hours). The optimum hydrogenation conditions will vary depending upon the type of catalyst selected for use and the reactivity of the anthraquinone salt, but may be readily determined by one skilled in the art with minimal experimentation based on the known art pertaining to anthraquinone hydrogenation. Typically, temperatures of from about 0° C. to 200° C. (preferably, 200° C. to 100° C.) and hydrogen pressures of from about 0.1 to 100 atmospheres (preferably, 0.5 to 10 atmospheres) will be appropriate for use. Preferably, the molar ratio of $H_2$ to anthraquinone salt is from about 1:1 to 4:1. The amount of catalyst employed is preferably sufficient to permit weight hourly space velocities of from 0.1 to 10 grams of anthraquinone salt per gram of catalyst per hour.

The hydrogenation step may be carried out in a batch, semi-batch, continuous, or semi-continuous manner using any suitable reaction vessel or apparatus wherein the anthraquinone salt may be intimately contacted with the transition metal hydrogenation catalyst and hydrogen. As the catalyst is normally heterogeneous in nature, fixed bed or slurry-type reactors are especially convenient for use. A trickle bed system may also be utilized.

FIG. 1 illustrates one embodiment of the integrated epoxidation process of this invention wherein a relatively light ethylenically unsaturated substrate such as propylene is epoxidized to yield a volatile epoxide. A stream comprised of sulfonic acid-substituted anthrahydroquinone alkyl ammonium salt and liquid medium (e.g., water, MeOH, water/MeOH) is passed via line 15 into oxidation zone 1 wherein the anthrahydroquinone salt is reacted with molecular oxygen to form an oxidation reaction product comprised of hydrogen peroxide, liquid medium, and the corresponding anthraquinone salt. The molecular oxygen is provided by air or pure or diluted oxygen introduced via line 2. Excess or unreacted molecular oxygen is removed via line 3. The salt is retained in zone 1 for a time sufficient to achieve at least 30% conversion to the anthraquinone.

The oxidation reaction product containing hydrogen peroxide passes from zone 1 via line 4 into zone 5. The ethylenically unsaturated substrate to be epoxidized is fed into zone 5 via line 6. The titanium silicalite catalyst is preferably deployed in zone 5 as a fixed bed. The resulting reaction mixture is maintained in zone 5 for a time and at a temperature sufficient to convert at least a portion of the substrate to epoxide, thereby consuming most of the hydrogen peroxide (preferably, more than 99% of the hydrogen peroxide is consumed). The epoxidation reaction mixture thus obtained passes through line 7 to separation zone 8 where it is separated by fractional distillation or other such means into a ethylenically unsaturated substrate stream (which may be returned to feed line 6 or epoxidation zone 5), an epoxide stream containing the desired epoxide product (withdrawn via line 10), and an anthraquinone stream comprised of the sulfonic acid-substituted anthraquinone alkyl ammonium salt generated during oxidation and liquid medium (withdrawn via line 11). It is desirable to remove that portion of the water generated as an epoxidation co-product in excess of that needed to dissolve the anthraquinone and anthrahydroquinone so that the water content in successive cycles does not continue to increase. The excess water may be removed by any suitable means such as distillation, either as a separate stream or together with the substrate and/or epoxide.

The aforementioned separation may, if desired, be carried out in stages. For example, if the substrate is propylene and the epoxide is propylene oxide, both the propylene and propylene oxide may be first separated together from the secondary alcohol by an initial distillation and then further fractionated into individual substrate and epoxide streams.

The anthraquinone stream from the separation zone is passed via line 11 to hydrogenation zone 13 wherein the stream is reacted with hydrogen (introduced via line 14) in the presence of a suitable hydrogenation catalyst such as a supported platinum, nickel, chromium, ruthenium, rhodium, or palladium catalyst (preferably deployed as a fixed bed in zone 13) so as to convert at least a portion, and preferably substantially all (e.g., over 95%), of the anthraquinone salt back to the anthrahydroquinone salt. The hydrogenated stream produced in zone 13 is passed via line 15 to oxidation zone 1. This integrated process is preferably operated in a continuous manner such that the desired epoxide is the only major organic product and the sulfonic acid-substituted anthraquinone alkylammonium salt is recycled.

From the foregoing description, one skilled in the art can readily ascertain the essential characteristics of this invention, and, without departing from the spirit and scope thereof, can make various changes and modifications of the invention to adapt it to various usages, conditions, and embodiments.

EXAMPLES

Several alkylammonium salts of anthraquinone-2,6-disulfonic acid were prepared starting with the commercially available disodium salt. For example, the tetrabutylammonium salt was obtained by dissolving the sodium salt into water and then adding 2 equivalents of tetrabutylammonium bromide. The resulting clear solution rapidly become turbid, yielding beige solids. The solids were collected by filtration, washed with water, and dried under vacuum to obtain the tetrabutylammonium salt.

The apparatus for the hydrogenation of the sulfonic-acid substituted anthraquinone salt consisted of a 50 ml Parr reactor equipped with a nitrogen inlet, hydrogen inlet, relief valve, overhead stirrer, fritted dip tube and thermocouple. Into the Parr reactor was introduced a mixture comprised of a heterogeneous hydrogenation catalyst (Raney nickel), solvent (varying ratios of methanol and water) and the bis (tetrabutylammonium) salt of anthraquinone-2,6-disulfonic acid. The mixture, once hydrogenated, was driven by use of nitrogen through the fritted dip tube (which retains the hydrogenation catalyst) into a separate apparatus wherein the hydrogenation product was oxidized. The oxidation apparatus consisted of a four neck 50 ml round bottom flask equipped with a condenser, nitrogen inlet, bubbler, air inlet, magnetic stirring bar, and stopper. The hydrogenation reaction product was oxidized in the presence of air, exhibiting a color change from caramel brown to pale yellow. The weight percent hydrogen peroxide in the resulting oxidation reaction product was then measured by iodometric titration.

The results obtained under varying conditions are shown in Table I. As may be seen, excellent selectivity to hydrogen peroxide was observed in many cases at moderately high conversions.

In another series of experiments, ruthenium on carbon (1% Ru) was evaluated as a hydrogenation catalyst in the process of the invention. The procedures used were similar to those described hereinabove. Good $H_2O_2$ selectivities were realized, as demonstrated in Table II. To further demonstrate the advantages of the present invention, the relative solubilities of various salts of anthraquinone-2,6-disulfonic acid in water and methanol were measured. The observed solubilities are reported in Table III. The alkylammonium salts were generally found to be much more soluble in both water and methanol than the sodium and ammonium salts suggested by the prior art to be useful as reactants in hydrogen peroxide processes. Table IV lists the solubilities of certain alkylammonium salts usable in the process of this invention in water/methanol mixtures of varying proportions.

To confirm that epoxidation may be selectively accomplished in the presence of the sulfonic acid-substituted anthraquinone alkylammonium salt, allyl alcohol was reacted with hydrogen peroxide at 60° C. using a TS-1 titanium silicalite as catalyst. Without anthraquinone salt present, 46% $H_2O_2$ conversion and 71% selectivity to glycidol (based on hydrogen peroxide) was observed in a control experiment. With the bis(tetrabutylammonium) salt of anthraquinone-2,6-disulfonic acid present, $H_2O_2$ conversion was 41% and 94% selectivity to the epoxide was attained. This demonstrates that the alkylammonium salt does not interfere with the desired epoxidation.

We claim:

1. A integrated process for producing an epoxide comprising
   (a) reacting a sulfonic acid-substituted anthrahydroquinone alkylammonium salt with molecular oxygen to form an oxidation reaction product comprised of hydrogen peroxide and a sulfonic acid-substituted anthraquinone alkylammonium salt;
   (b) contacting the oxidation reaction product with an ethylenically unsaturated substrate and a catalytically effective amount of a titanium silicalite to form an epoxidation reaction mixture comprised of a sulfonic acid-substituted anthraquinone alkylammonium salt and the epoxide;
   (c) separating the epoxide from the sulfonic acid-substituted anthraquinone alkylammonium salt;
   (d) reacting the sulfonic acid-substituted anthraquinone alkylammonium salt with hydrogen in the presence of a transition metal-containing hydrogenation catalyst to convert the sulfonic acid-substituted anthraquinone alkylammonium salt to the sulfonic acid-substituted anthrahydroquinone alkylammonium salt; and
   (e) recycling the sulfonic acid-substituted anthrahydroquinone alkylammonium salt from step (d) for use in step (a).

2. The process of claim 1 wherein the ethylenically unsaturated substrate is a $C_2-C_{10}$ aliphatic olefin.

3. The process of claim 1 wherein the titanium silicalite has an MFI, MEL, or zeolite beta topology.

4. The process of claim 1 wherein the titanium silicalite has a composition corresponding to the chemical formula $$xTiO_2:(1-x)SiO_2$$

wherein x is from 0.01 and 0.125.

5. The process of claim 1 wherein said process is carried out continuously.

6. The process of claim 1 wherein the titanium silicalite is deployed in the form of a fixed bed.

7. The process of claim 1 wherein the titanium silicalite is deployed in the form of a slurry.

8. The process of claim 1 wherein the ethylenically unsaturated substrate is propylene and the epoxide is propylene oxide.

9. The process of claim 1 wherein separation step (c) is accomplished by distillation.

10. The process of claim 1 wherein the sulfonic acid-substituted anthrahydroquinone alkylammonium salt has the structure

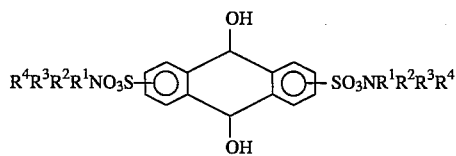

wherein $R^1$, $R^2$, $R^3$, and $R^4$ are the same or different and are selected from the group consisting of hydrogen and $C_1-C_6$ alkyl, subject to the proviso that each N is substituted with at least one $C_1-C_6$ alkyl.

11. The process of claim 10 wherein $R^1$, $R^2$, $R^3$, and $R^4$ contain a total of from 4 to 16 carbon atoms.

12. The process of claim 1 wherein step (a) is performed in a liquid medium.

13. The process of claim 12 wherein said liquid medium comprises a polar protic solvent.

14. The process of claim 13 wherein said polar protic solvent is selected from the group consisting of water, $C_1-C_6$ aliphatic alcohols, and mixtures thereof.

15. The process of claim 1 wherein step (a) is performed at a partial oxygen pressure of 5 to 200 psia.

16. The process of claim 1 wherein step (a) is performed at a temperature of from 0° C. to 120° C.

17. The process of claim 1 wherein step (b) is performed at a temperature of from 0° C. to 120° C.

18. The process of claim 1 wherein the transition metal in the hydrogenation catalyst is selected from palladium, platinum, ruthenium, chromium, rhodium, and nickel.

19. The process of claim 1 wherein step (d) is performed at a temperature of 20° C. to 200 ° C.

20. The process of claim 1 wherein step (d) is performed at a hydrogen pressure of 0.1 to 100 atmospheres.

21. An integrated process for producing a $C_2-C_{10}$ aliphatic epoxide comprising
   (a) reacting a sulfonic acid-substituted anthrahydroquinone alkylammonium salt having the structure

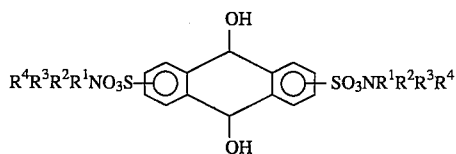

wherein $R^1$, $R^2$, $R^3$, and $R^4$ are the same or different and are selected from the group consisting of hydrogen and $C_1-C_6$ alkyl, subject to the proviso that each N is substituted with at least one $C_1-C_6$ alkyl, with molecular oxygen in a liquid medium comprised of a polar protic solvent at a temperature of from 20° C. to 60° C. and a partial oxygen pressure of 5 to 200 psia to form an oxidation reaction product comprised of hydrogen peroxide and a sulfonic acid-substituted anthraquinone alkylammonium salt corresponding to the sulfonic acid-substituted anthrahydroquinone alkylammonium salt;
   (b) contacting the oxidation reaction product with a $C_2-C_{10}$ aliphatic olefin and a catalytically effective amount of a titanium silicalite having an MFI, MEL, or zeolite beta topology at a temperature of from 30° C. to 90° C. to form an epoxidation reaction mixture comprised of the sulfonic acid-substituted anthraquinone alkylammonium salt and the $C_2-C_{10}$ aliphatic epoxide;
   (c) separating the $C_2-C_{10}$ aliphatic epoxide from the sulfonic acid-substituted anthraquinone alkylammonium salt by distillation;

(d) reacting the sulfonic acid-substituted anthraquinone alkylammonium salt with hydrogen in the presence of a heterogeneous hydrogenation catalyst comprised of a transition metal selected from palladium, platinum, ruthenium, chromium, rhodium and nickel, at a temperature of 20° C. to 100 ° C. and a hydrogen pressure of 0.5 to 10 atmospheres to convert the sulfonic acid-substituted anthraquinone alkylammonium salt to the sulfonic acid-substituted anthrahydroquinone alkylammonium salt; and (e) recycling the sulfonic acid-substituted anthrahydroquinone alkylammonium salt from step (d) for use in step (a).

22. The integrated process of claim 21 wherein the polar protic solvent is selected from the group consisting of water, $C_1$–$C_6$ aliphatic alcohols, and mixtures thereof.

23. The integrated process of claim 21 wherein $R^1$, $R^2$, $R^3$, and $R^4$ contain a total of from 4 to 16 carbon atoms.

24. The integrated process of claim 21 wherein the sulfonic acid-substituted anthrahydroquinone alkylammonium salt is a 2,6 or 2,7 isomer.

* * * * *